(12) United States Patent
Henry et al.

(10) Patent No.: US 9,995,613 B2
(45) Date of Patent: Jun. 12, 2018

(54) CORIOLIS FREQUENCY TRACKING

(71) Applicant: Invensys Systems, Inc., Foxboro, MA (US)

(72) Inventors: Manus P. Henry, Oxford (GB); Mihaela D. Duta, Oxford (GB); Michael S. Tombs, Oxford (GB)

(73) Assignee: Schneider Electric Systems USA, Inc., Foxboro, MA (US)

( * ) Notice: Subject to any disclaimer, the term of this patent is extended or adjusted under 35 U.S.C. 154(b) by 902 days.

(21) Appl. No.: 14/268,802

(22) Filed: May 2, 2014

(65) Prior Publication Data

US 2014/0238149 A1 Aug. 28, 2014

Related U.S. Application Data

(63) Continuation of application No. 12/044,754, filed on Mar. 7, 2008, now Pat. No. 8,751,171.

(60) Provisional application No. 60/893,573, filed on Mar. 7, 2007.

(51) Int. Cl.
| | | |
|---|---|---|
| *G01F 1/84* | (2006.01) | |
| *G01F 1/76* | (2006.01) | |
| *G01N 9/00* | (2006.01) | |
| *G01F 15/02* | (2006.01) | |

(52) U.S. Cl.
CPC ............ *G01F 1/849* (2013.01); *G01F 1/8436* (2013.01); *G01F 1/8486* (2013.01); *G01F 15/024* (2013.01); *G01N 9/002* (2013.01)

(58) Field of Classification Search
CPC ......... G01N 9/002; G01F 1/8486; G01F 1/84; G01F 1/76; G01F 1/78; G01F 1/80–1/88; G01F 15/024; G01C 19/56; G01R 23/14; G01R 23/145; G01J 9/04; G01B 9/02003
See application file for complete search history.

(56) References Cited

U.S. PATENT DOCUMENTS

| | | | | |
|---|---|---|---|---|
| 5,228,327 A | * | 7/1993 | Bruck | G01F 1/8413 702/45 |
| 5,804,741 A | * | 9/1998 | Freeman | G01F 1/8413 702/190 |
| 6,160,959 A | * | 12/2000 | Mizumoto | G03B 5/00 396/52 |

(Continued)

OTHER PUBLICATIONS

Tombs et al., "High precision Coriolis mass flow measurement applied to small volume proving," 17 Flow Measurement and Instrumentation, 371-382 (2006).*

*Primary Examiner* — Patrick King
(74) *Attorney, Agent, or Firm* — Stephen Manetta; Ralph Graham; Senniger Powers

(57) ABSTRACT

Motion is induced in a conduit such that the conduit vibrates in a major mode of vibration having a major amplitude and a minor mode of vibration having a minor amplitude. The major amplitude is larger than the minor amplitude, the major mode of vibration has a first frequency of vibration and the minor mode of vibration has a second frequency of vibration, and the minor mode of vibration interferes with the major mode of vibration to cause a beat signal having a frequency related to the first frequency of vibration and the second frequency of vibration. The frequency of the beat signal is determined, and the second frequency of vibration is determined based on the determined frequency of the beat signal.

8 Claims, 8 Drawing Sheets

(56) References Cited

U.S. PATENT DOCUMENTS

| | | | | |
|---|---|---|---|---|
| 6,378,364 B1* | 4/2002 | Pelletier | ............... | E21B 47/06 |
| | | | | 73/152.47 |
| 6,705,172 B1* | 3/2004 | Deppe | ............... | G01F 1/8431 |
| | | | | 73/861.355 |
| 6,993,445 B2* | 1/2006 | Clarke | ............... | G01F 1/329 |
| | | | | 702/106 |
| 2005/0109123 A1* | 5/2005 | Cheesewright | ....... | G01F 1/8436 |
| | | | | 73/861.355 |
| 2005/0274200 A1* | 12/2005 | Henry | ............... | G01F 1/8431 |
| | | | | 73/861.356 |

* cited by examiner

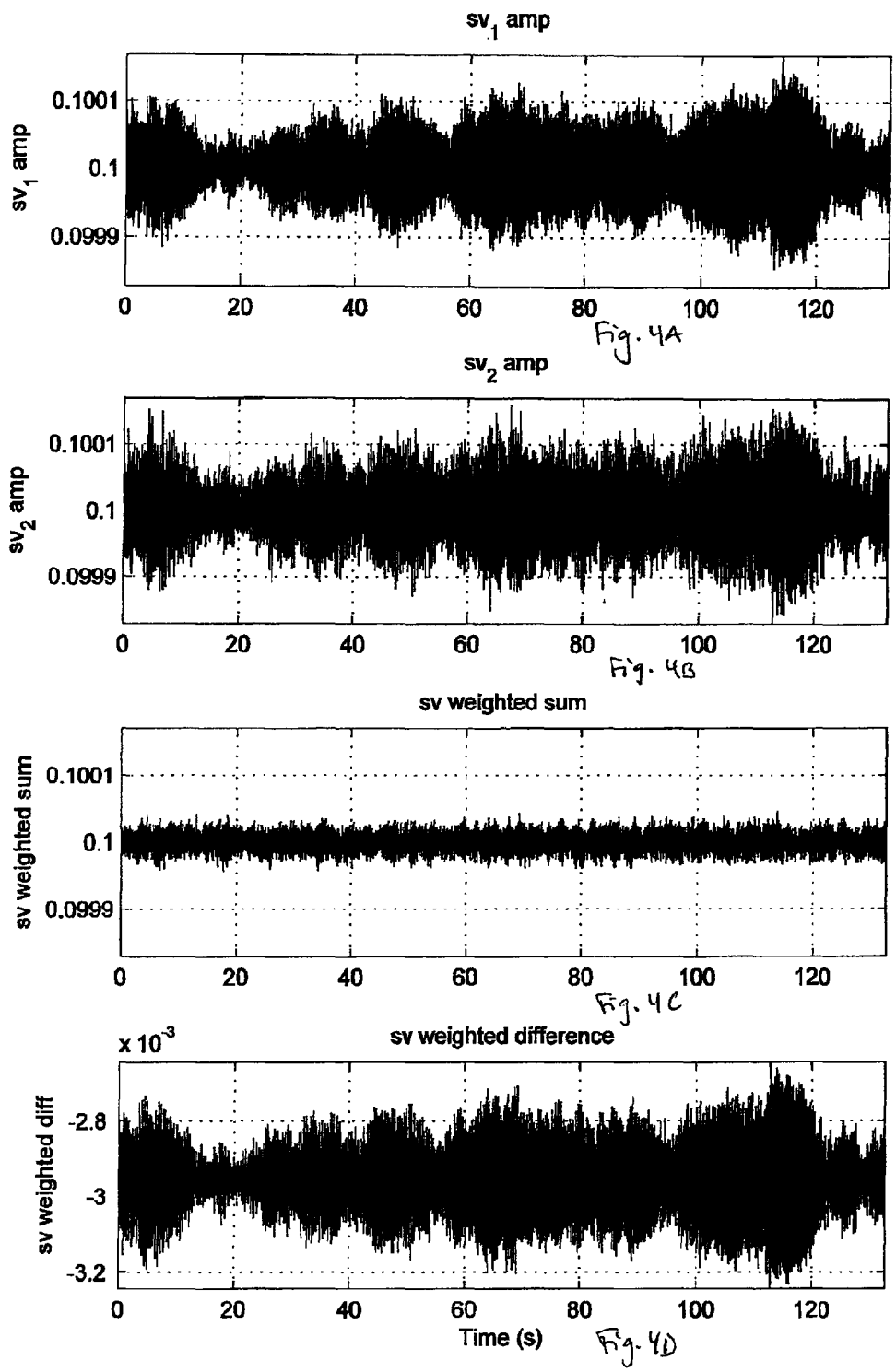

CORIOLIS FREQUENCY TRACKING

CROSS-REFERENCE TO RELATED APPLICATIONS

This application is a continuation of U.S. application Ser. No. 12/044,754, filed Mar. 7, 2008, and titled CORIOLIS FREQUENCY TRACKING, which claims the benefit of U.S. Provisional Application Ser. No. 60/893,573, filed Mar. 7, 2007, titled CORIOLIS FREQUENCY TRACKING, the entire contents of which are each hereby incorporated by reference.

TECHNICAL FIELD

This description relates to flowmeters.

BACKGROUND

Flowmeters provide information about materials being transferred through a conduit. For example, mass flowmeters provide a measurement of the mass of material being transferred through a conduit. Similarly, density flowmeters, or densitometers, provide a measurement of the density of material flowing through a conduit. Mass flowmeters also may provide a measurement of the density of the material.

For example, Coriolis-type mass flowmeters are based on the Coriolis effect, in which material flowing through a rotating conduit is affected by a Coriolis force and therefore experiences an acceleration. Many Coriolis-type mass flowmeters induce a Coriolis force by sinusoidally oscillating a conduit about a pivot axis orthogonal to the length of the conduit. In such mass flowmeters, the Coriolis reaction force experienced by the traveling fluid mass is transferred to the conduit itself and is manifested as a deflection or offset of the conduit in the direction of the Coriolis force vector in the plane of rotation.

SUMMARY

In one general aspect, motion is induced in a conduit such that the conduit vibrates in a major mode of vibration having a major amplitude and a minor mode of vibration having a minor amplitude. The major amplitude is larger than the minor amplitude, the major mode of vibration has a first frequency of vibration and the minor mode of vibration has a second frequency of vibration, and the minor mode of vibration interferes with the major mode of vibration to cause a beat signal having a frequency related to the first frequency of vibration and the second frequency of vibration. The frequency of the beat signal is determined, and the second frequency of vibration is determined based on the determined frequency of the beat signal.

Implementations may include one or more of the following features. Determining the frequency of the beat signal may include determining a first time at which an amplitude of the beat signal has a predefined value and a second time at which the amplitude of the beat signal has the predefined value, determining a difference between the first time and the second time, and determining the frequency of the beat signal based on the difference. The predefined value may be zero such that the determined frequency of the beat signal may be based on zero-crossings of the beat signal. The first time and second time may include non-consecutive occurrences of the predefined value. The beat signal may be interpolated, and determining the first time and the second time may include determining the first time and second time based on the interpolated beat signal. The major mode of vibration may be a driven mode, and the minor mode of vibration may be a Coriolis mode. The first frequency of vibration may be a driven mode frequency, and the second frequency of vibration may be a Coriolis mode frequency.

In some implementations, the first frequency of vibration based on the determined frequency of the beat signal may include determining the Coriolis mode frequency by adding the frequency of the beat signal to the driven mode frequency. The beat signal may be determined, where determining the beat signal may include receiving a first sensor signal from a first motion sensor and a second sensor signal from a second motion sensor, the first and second motion sensors configured to sense a motion of the conduit, and determining a difference signal by subtracting the first sensor signal from the second sensor signal. A first amplitude signal associated with the first sensor signal may be determined and a second amplitude signal associated with the second sensor signal may be determined. The first amplitude signal or the second amplitude signal may be adjusted such that the first and second amplitude signals have mean amplitudes that are substantially the same.

In some implementations, the difference signal may be filtered. Filtering the difference signal may include filtering the difference signal with a band-pass filter. Filtering the difference signal with the band-pass filter may include filtering the difference signal with a band-pass filter that has a frequency band determined based on an expected frequency range of the difference signal. The conduit may be configured to receive a fluid, and the at least one property of the fluid may be determined based on the determined frequency. The at least one property may include one or more of a density of the fluid and a mass flowrate of the fluid.

Implementations of any of the techniques described above may include a method or process, a system, a flowmeter, instructions stored on a storage device of flowmeter transmitter, or code segments stored on a computer-readable medium storing a computer program. The details of particular implementations are set forth in the accompanying drawings and description below. Other features will be apparent from the following description, including the drawings, and the claims.

BRIEF DESCRIPTION OF THE DRAWINGS

FIGS. 4A-4D illustrate example amplitude data for a power spectra.

DETAILED DESCRIPTION

Types of flowmeters include digital flowmeters. For example, U.S. Pat. No. 6,311,136, which is hereby incorporated by reference, discloses the use of a digital flowmeter and related technology including signal processing and measurement techniques. Such digital flowmeters may be very precise in their measurements, with little or negligible noise, and may be capable of enabling a wide range of positive and negative gains at the driver circuitry for driving the conduit. Such digital flowmeters are thus advantageous in a variety of settings. For example, commonly-assigned U.S. Pat. No. 6,505,519, which is incorporated by reference, discloses the use of a wide gain range, and/or the use of negative gain, to prevent stalling and to more accurately exercise control of the flowtube (even during difficult conditions such as two-phase flow, e.g., a flow containing a mixture of liquid and gas). The flowtube also may be referred to as a conduit.

Although digital flowmeters are specifically discussed below with respect to, for example, FIGS. 1A, 1B, and 2, it should be understood that analog flowmeters also exist. Although such analog flowmeters may be prone to typical shortcomings of analog circuitry, e.g., low precision and high noise measurements relative to digital flowmeters, they also may be compatible with the various techniques and implementations discussed herein. Thus, in the following discussion, the term "flowmeter" or "meter" is used to refer to any type of device and/or system in which a flowmeter system uses various control systems and related elements to measure a mass flow, density, and/or other parameters of a material(s) moving through a flowtube or other conduit.

Figure 1A:
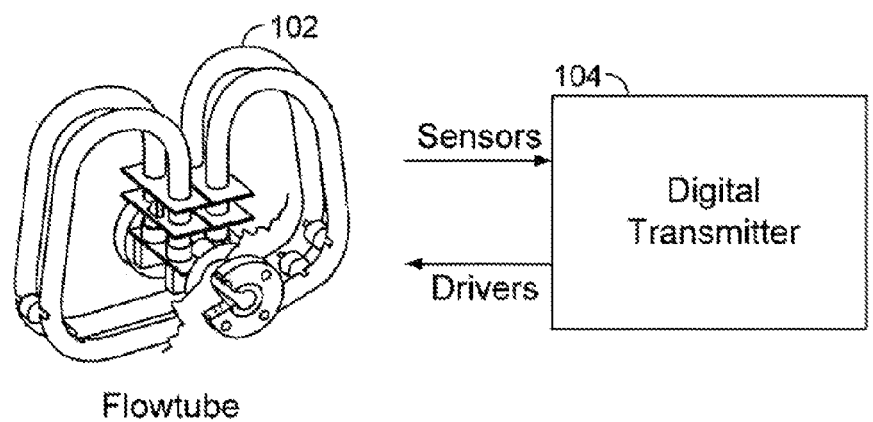
FIG. 1A is an illustration of a Coriolis flowmeter using a bent flowtube.

FIG. 1A is an illustration of a digital flowmeter using a bent flowtube 102 and a digital transmitter 104. Specifically, the bent flowtube 102 may be used to measure one or more physical characteristics of, for example, a (traveling or non-traveling) fluid, as referred to above. The digital transmitter 104 exchanges sensor and drive signals with the bent flowtube 102, so as to both sense an oscillation of the bent flowtube 102, and to drive the oscillation of the bent flowtube 102 accordingly. By quickly and accurately determining the sensor and drive signals, the digital transmitter 104, as referred to above, provides for fast and accurate operation of the bent flowtube 102. Examples of the digital transmitter 104 being used with a bent flowtube are provided in, for example, commonly-assigned U.S. Pat. No. 6,311,136.

Figure 1B:
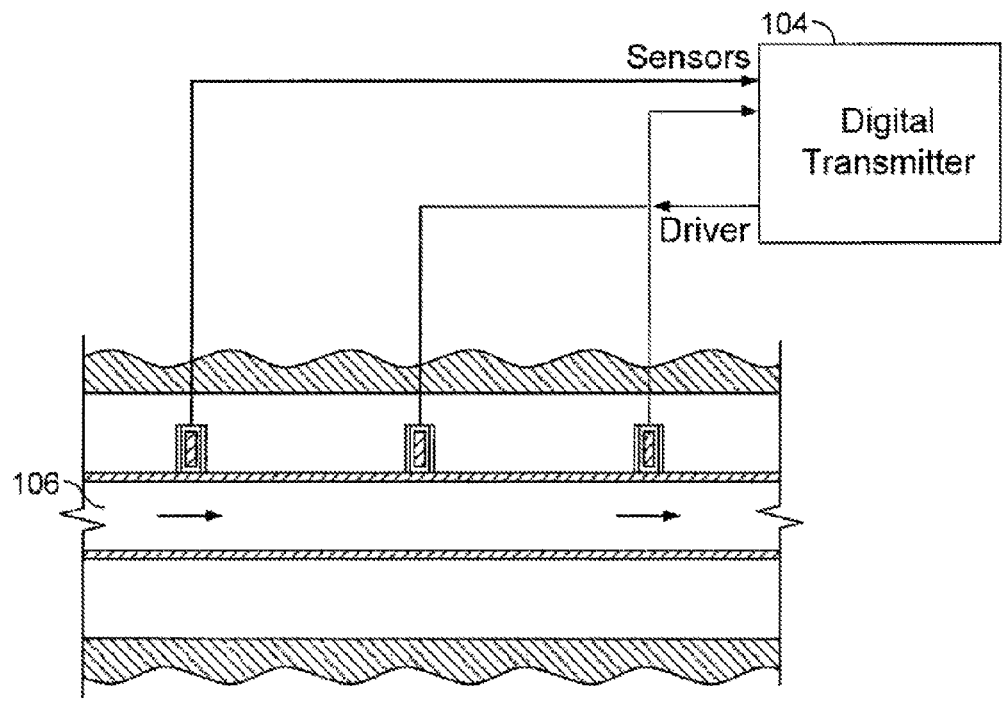
FIG. 1B is an illustration of a Coriolis flowmeter using a straight flowtube.

FIG. 1B is an illustration of a digital flowmeter using a straight flowtube 106. More specifically, in FIG. 1B, the straight flowtube 106 interacts with the digital transmitter 104. Such a straight flowtube operates similarly to the bent flowtube 102 on a conceptual level, and has various advantages/disadvantages relative to the bent flowtube 102. For example, the straight flowtube 106 may be easier to (completely) fill and empty than the bent flowtube 102, simply due to the geometry of its construction. In operation, the bent flowtube 102 may operate at a frequency of, for example, 50-110 Hz, while the straight flowtube 106 may operate at a frequency of, for example, 300-1,000 Hz. The bent flowtube 102 represents flowtubes having a variety of diameters, and may be operated in multiple orientations, such as, for example, in a vertical or horizontal orientation.

Figure 2:
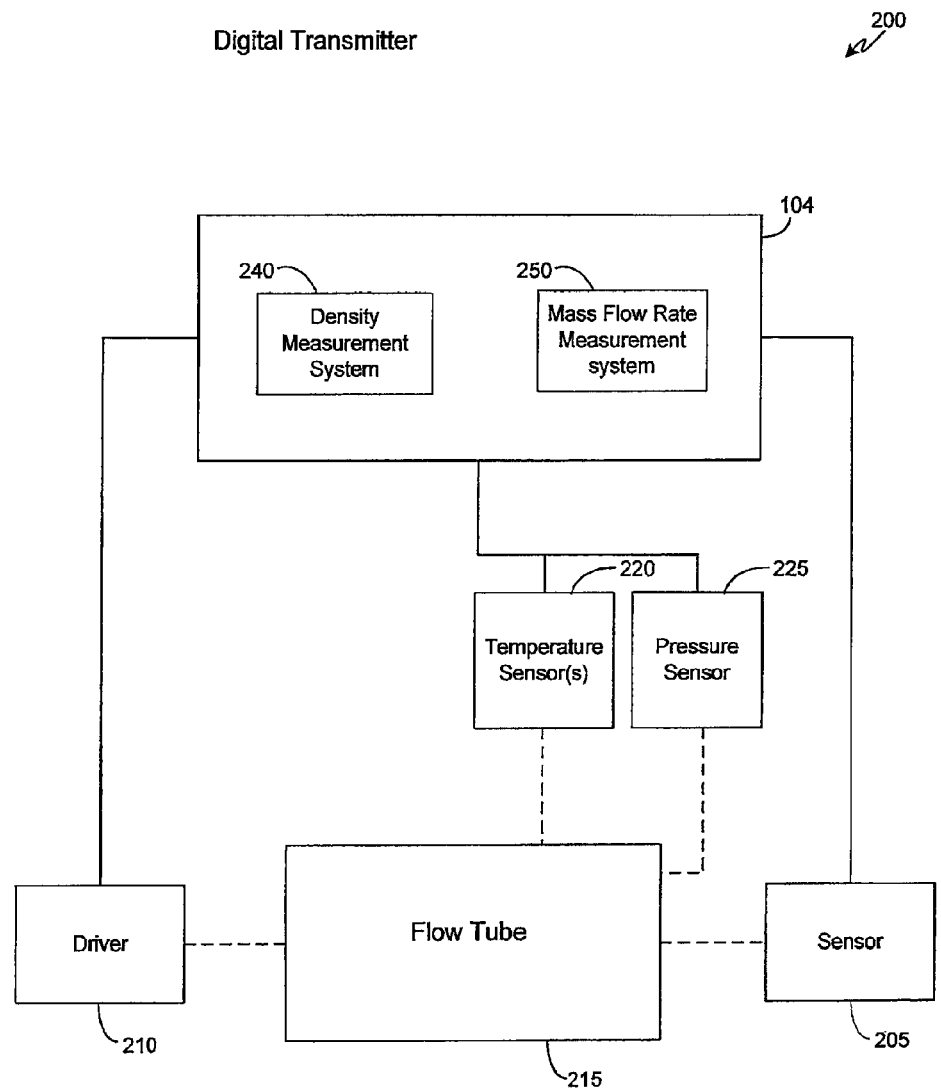
FIG. 2 is a block diagram of a digital mass flowmeter for measuring a property of a fluid.

Referring to FIG. 2, a digital mass flowmeter 200 includes the digital transmitter 104, one or more motion sensors 205, one or more drivers 210, a flowtube 215 (which also may be referred to as a conduit, and which may represent either the bent flowtube 102, the straight flowtube 106, or some other type of flowtube), and a temperature sensor 220. The digital transmitter 104 may be implemented using one or more of, for example, a processor, a Digital Signal Processor (DSP), a field-programmable gate array (FPGA), an ASIC, other programmable logic or gate arrays, or programmable logic with a processor core. It should be understood that, as described in U.S. Pat. No. 6,311,136, associated digital-to-analog converters may be included for operation of the drivers 210, while analog-to-digital converters may be used to convert sensor signals from the sensors 205 for use by the digital transmitter 104.

The digital transmitter 104 generates a measurement of, for example, density and/or mass flow rate of a material flowing through the flowtube 215, based at least on signals received from the motion sensors 205. The digital transmitter 104 also controls the drivers 210 to induce motion in the flowtube 215. This motion is sensed by the motion sensors 205.

Density measurements of the material flowing through the flowtube are related to, for example, the frequency of the motion of the flowtube 215 that is induced in the flowtube 215 (typically the resonant frequency) by a driving force supplied by the drivers 210, and/or to the temperature of the flowtube 215. Similarly, mass flow through the flowtube 215 is related to the phase and frequency of the motion of the flowtube 215, as well as to the temperature of the flowtube 215.

The temperature in the flowtube 215, which is measured using the temperature sensor 220, affects certain properties of the flowtube, such as its stiffness and dimensions. The digital transmitter 104 may compensate for these temperature effects. Also in FIG. 2, a pressure sensor 225 is in communication with the transmitter 104, and is connected to the flowtube 215 so as to be operable to sense a pressure of a material flowing through the flowtube 215.

A flowtube that has two drivers can be driven in either of the first two natural modes of vibration. The flowtube is forced to oscillate in one 'driven mode', and the effect of Coriolis forces cause a movement in the second 'Coriolis mode'. Thus, the first mode of vibration may correspond to the 'Coriolis mode,' and the second mode of vibration may correspond to the 'driven mode.' Alternatively, the first mode of vibration may correspond to the 'driven mode,' and the second mode of vibration may correspond to the 'Coriolis mode.' The driven mode also may be referred to as the major mode, and the Coriolis mode also may be referred to as the minor mode. The amplitude of vibration of the major mode may be referred to as the major amplitude, and the amplitude of vibration of the minor mode may be referred to as the minor amplitude. The amplitude of the major mode is greater than the amplitude of the minor mode.

The frequency of vibration in the Coriolis mode may be referred to as the Coriolis mode frequency, k, and the frequency of vibration in the driven mode may be referred to as the driven mode frequency, f. In some implementations, the driven mode frequency is higher than the Coriolis mode frequency. However, physical characteristics of the flowtube 215 may cause the Coriolis mode frequency to be higher than the driven mode frequency. The effect of Coriolis forces also may produce a Coriolis mode wave shape at the driven mode frequency, f. The Coriolis mode wave shape, resonating at the driven mode frequency, f, that is caused by the Coriolis forces may be referred to as a 'measurement mode'.

In some implementations, the flowtube may be driven by just one driver. The driver may be placed at the midpoint of the flowtube. In these implementations, the flowtube is actively driven in the first mode of vibration only. In the first mode of vibration, the maximum amplitude of vibration is at the midpoint (e.g., where the driver is placed). However, for the second mode of vibration, a point of minimum amplitude of vibration may occur at the midpoint, thus implementations with one driver located at the midpoint of the flowtube generally cannot drive the flowtube in the second mode of vibration. In some implementations that include one driver, the driver may be appropriately placed between the midpoint of the flowtube and an end of the flowtube, at a position where the amplitude of the second mode is maximum, so that the single driver may be able to drive the flowtube in the second mode of vibration.

In implementations that include two drivers, the two drivers may be placed, for example, at the positions on the flowtube that are half-way between the midpoint of the flowtube and the ends of the flowtube. In these implementations, the drivers may drive the flowtube in the first mode of vibration when the drivers produce drive signals that are in phase with each other. In these implementations, the two drivers may be located at the positions corresponding to the locations of the maximum amplitude of the second mode of vibration. Thus, when the drive signals produced by the two drivers are 180-degrees out of phase with each other, the two drivers can drive the flowtube at the second mode of vibration. When the flowtube is driven in the second mode of vibration in this manner, the Coriolis mode has a lower frequency than the driven mode. Accordingly, implementations including more than one driver provide an extra degree of freedom and allow a choice between whether the Coriolis mode has a lower frequency than the driven mode.

In some implementations, the flowtube may be attached to a torsion rod that holds the mass of the flowtube. The torsion rod may stabilize the flowtube and minimize stress on the flowtube (e.g., as the flowtube is twisted by the out-of-phase drive signals from the drivers). The torsion rod may be used with flowtubes having a relatively large cross-sectional diameter. For example, the torsion rods may be used with flowtubes having diameters of 6-inches (or 15.24-centimeters) or greater. An example of such a flowtube is the Rheonik Mass Flowmeter available from RHEONIK GmbH of Germany. The stiffness and mass distribution of the torsion bar has a strong influence on the driven mode frequency.

In implementations that use a torsion bar, the flowtube is attached to two drivers that produce drive signals that are 180-degrees out of phase with each other. Because the drive signals are out-of-phase, the driven mode frequency is the lowest asymmetric mode of vibration. However, the torsion bar may be weighted such that the Coriolis mode, which in this arrangement is the lowest symmetric mode of vibration, may have a frequency that is lower or higher than that of the driven mode. Additionally, the frequencies of the driven mode and the Coriolis mode may be adjusted by weighting the torsion bar. For example, the frequency of the driven mode and the Coriolis mode may be made to be closer together or further apart due to the weighting. The rest of this document describes one or more techniques for tracking the Coriolis frequency by observing the effect of Coriolis noise on the calculated amplitude of oscillation or phase difference. In particular, the techniques may enable estimates of the Coriolis mode frequency, potentially without recourse to the intensive computing associated with fast Fourier transform (FFT) calculations of high bandwidth data. For instance, in one implementation, a beat signal is created in which a beat frequency between a Coriolis mode frequency and a driven mode frequency is deliberately enhanced. Tracking of the zero crossings in this beat frequency may lead to an estimate of the beat frequency, which leads to an estimate of the Coriolis mode frequency.

Oscillations at the Coriolis mode frequency, k, may interfere with the driven mode frequency, f, which may result in a beat signal with a frequency of k–f (as demonstrated when amplitude and phase data is calculated using Fourier techniques). This interference results in a noise signal, which may be referred to as a beat frequency signal. The "beating" effect of low amplitude Coriolis noise on the calculated amplitude and phase difference has been described in, for example, U.S. Pat. No. 7,313,488 and U.S. Pat. No. 6,311,136. Both U.S. Pat. No. 7,313,488 and U.S. Pat. No. 6,311,136 are incorporated by reference.

Typically, the Coriolis noise amplitude has a Brownian motion, which is observable as a distinct envelope around the uncorrected phase difference between the sensor signals (such as the motion sensors 205) and amplitude measurements. The Coriolis noise on the amplitude signal may be 90 degrees out of phase with that Coriolis noise on the phase difference signal. Thus, assuming all observed amplitude change is Coriolis noise, that rate of change of amplitude may be in phase with and proportional to the Coriolis noise on the phase difference. A correction factor proportional to the rate of change of amplitude may thus be used to reduce the Coriolis noise on the phase difference. Additionally, because the Coriolis mode and the driven mode have different mode shapes, the Coriolis noise may be 180 degrees out of phase between the two sensor signals.

A signal may be created in which the beat frequency between the Coriolis mode frequency and the driven mode frequency is deliberately enhanced. Tracking of the zero crossings in this signal can lead to an estimate of the beat frequency, which may lead to an estimate of the Coriolis frequency. Tracking of the zero crossings may be referred to as "beat frequency tracking."

A number of signals may be used to perform the beat frequency tracking. In the example described below, the two sensor signals are used. The sensor signals may be from sensors such as the motion sensors 205 discussed above, and the sensor signals may include information such as amplitude of oscillation of a conduit such as the flowtube 215. The calculations in the example described below are based on amplitude updates that occur at every half-cycle of the driven mode frequency. The driven mode frequency may be, for example, 150 Hz. The various techniques described in this document may or may not calculate or derive high frequency (e.g., 10 KHz) motion signals in which the various modes of vibration are predominant, in order to track the Coriolis mode frequency.

Figure 3A:
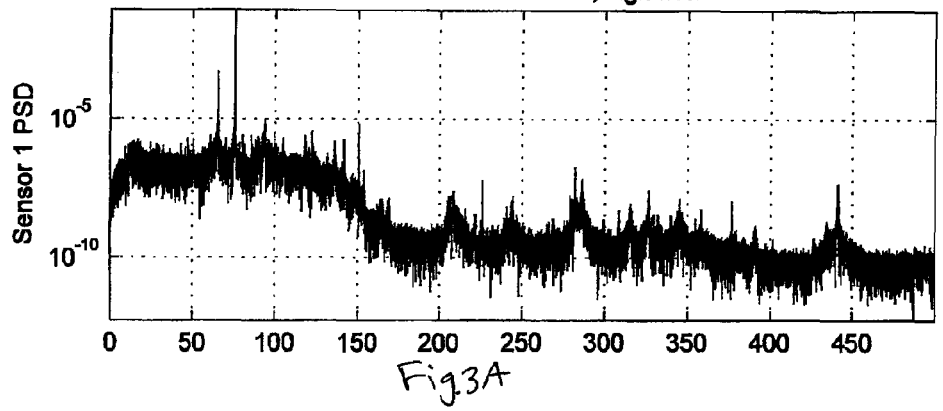
FIGS. 3A-3C illustrate example power spectra based on signals received from sensors configured to sense motion of a flowtube.
Figure 3B:
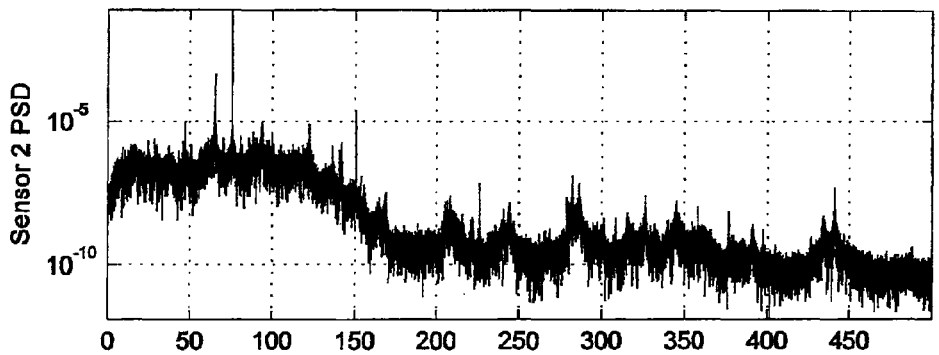
Figure 3C:
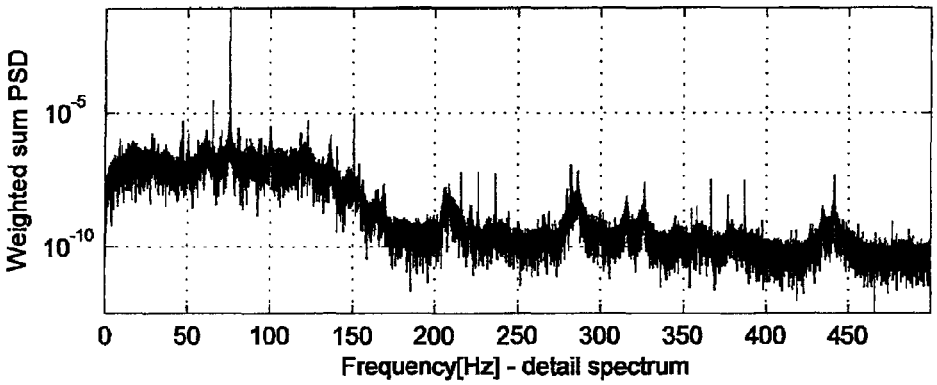

FIGS. 3A-3C show the power spectral density (PSD) of typical sensor spectra (at 10 kHz) data taken from a 6" (15.2 centimeters) flowmeter with a high flow. A 6" flowmeter may be a conduit with a cross-sectional diameter of 6". A high flow may be a mass flow rate of 25-30 kg/s, for example. In other examples, a conduit with a larger cross-sectional diameter may be used. For example, the cross-sectional diameter of the conduit may be 8" to 12".

In particular, FIG. 3A shows the PSD of a signal from a first motion sensor, and FIG. 3B shows the PSD of a signal from a second motion sensor. The first and second motion sensors may be the motion sensors 205 described above. FIG. 3C shows the PSD of the weighted sum of the signals from the first and second sensors 205. As discussed below, the signals from the first and second sensors 205 are weighted to ensure that the signals have the same average amplitude before the signals are added together. A low pass filter has been applied to the sensor signals using, for example, an FPGA in the digital transmitter 104, to reduce the harmonic content above 180 Hz.

As seen in the example shown in FIGS. 3A-3C, the spectra are dominated by two frequencies, the driven mode frequency at about 75 Hz and the Coriolis mode frequency at about 65 Hz. The weighted sum, which also may be referred to as the weighted mean, of the sensor data is the sum of the signals from the first and second sensors 205. One or both of the signals from sensors 205 may be multiplied by a gain factor. The gain factor, which also may be referred to as the sensor balance, ensures that the signals from the first and second sensors 205 have identical mean amplitudes prior to calculating the weighted sum. The sensor balance may be, for example, the ratio of an amplitude of a signal from the first sensor 205 and an amplitude of a signal from the second sensor 205.

For the example shown in FIGS. 3A-3C, Table 1 includes the properties that may be derived from the spectral analysis.

TABLE 1

| Signal | Driven mode | | Coriolis Mode | |
|---|---|---|---|---|
| | Frequency | Amplitude | Frequency | Amplitude |
| First sensor | 75.3835 Hz | 0.08196 V | 65.1657 Hz | 0.000484 V |
| Second sensor | 75.3835 Hz | 0.08196 V | 65.1657 Hz | 0.000473 V |
| Weighted sum | 75.3835 Hz | 0.08196 V | 65.1657 Hz | 0.000030 V |

As seen in the Coriolis mode data presented in Table 1, the Coriolis mode is reduced by an order of magnitude in the weighted sum signal as compared to the first and second sensor signals. This is a result of the fact that the Coriolis mode contribution is 180 degrees out of phase between the first and second sensors, as discussed above.

FIGS. 4A-4D illustrate the amplitude data for the data set shown in FIGS. 3A-3C. In particular, FIG. 4A shows the amplitude of the signal from the first sensor 205 (SV1) and FIG. 4B shows the amplitude of the signal from the second sensor 205 (SV2). The amplitudes are calculated using a standard Fourier technique based on the driven mode frequency, as described in, for example, U.S. Pat. No. 6,311,136. In the example shown, SV2 has been weighed by the gain factor. As described with respect to FIGS. 3A-3C, applying the gain factor to SV1 and/or SV2 ensures that SV1 and SV2 have equal average amplitudes. The measurement of the sensor signals SV1 and SV2 is updated twice every drive cycle, or at approximately 150 Hz, in the example shown in FIGS. 4A-4D.

As seen in FIGS. 4A and 4B, there is a strong correlation between the signals from the two sensors 205, which would be expected if the physical oscillation of the flowtube 215 was varying and the oscillation was being measured by the two sensors 205. However, the observed variation in amplitude is due mostly to the effect of Coriolis noise rather than variation in the physical oscillation of the flowtube 215. The strong negative correlation of the amplitude signals from the sensors 205 is evidence of the effect of Coriolis noise and is caused by the different mode shape of the Coriolis mode as compared to the driven mode. The difference in the mode shapes is apparent in FIG. 4C, which shows the weighted sum of the amplitudes of the two sensor signals, SV1 and SV2, over the same time period. The noise in the amplitude signals has been reduced by approximately a factor of four because the Coriolis mode contributions to the two signals, which are 180 degrees out of phase with each other, are cancelled out.

FIG. 4D shows the weighted difference between the amplitudes of the sensor signals, SV1 and SV2. In contrast to the weighted sum shown in FIG. 4C, the weighted difference of the two sensor signals has an enhanced Coriolis mode contribution. The dominant frequency of the weighted difference signal is the beat frequency between the Coriolis mode and the driven mode, which is the difference between the Coriolis mode frequency and the driven mode frequency. The weighted difference signal may be used to track the Coriolis mode frequency as any genuine change in amplitude will be present in both SV1 and SV2 and is thus removed from the weighted difference signal.

Figure 5:
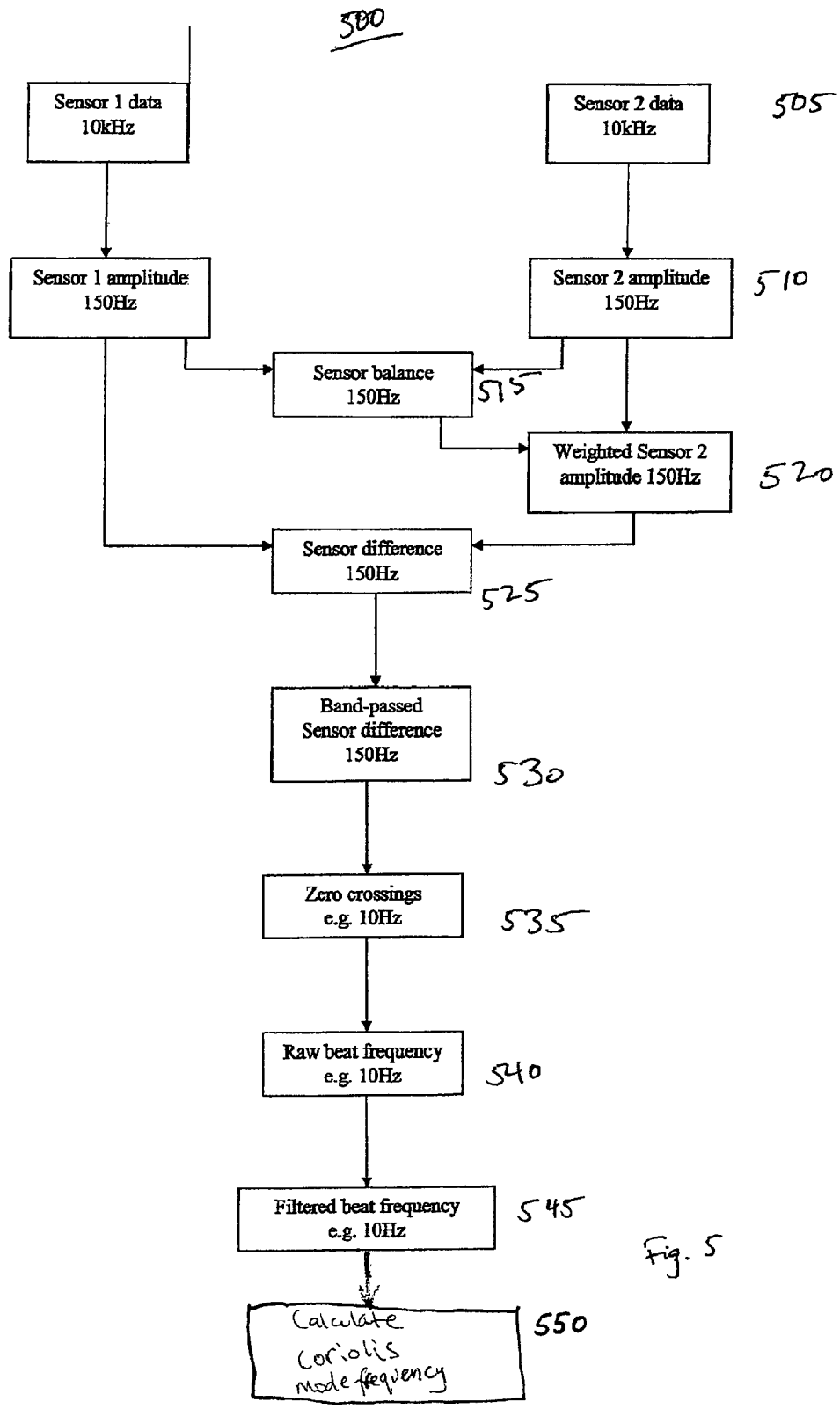
FIG. 5 is an example process for determining a beat frequency.

FIG. 5 shows an example process 500 for calculating the beat frequency between the Coriolis mode frequency and the driven mode frequency based on the weighted difference signal between the signals from the sensors 205. The process 500 may be performed by a processor on the digital transmitter 104. The weighted difference signal may be, for example, the weighted difference signal described with respect to FIG. 4D.

Raw data from the motion sensors 205 is received (505). In the example process 500, the signals are from a first motion sensor 205 and a second motion sensor 205, and the raw sensor data is sampled at an update rate of 10 kHz. The amplitudes of the signals are determined using standard Fourier techniques (510). Using the gain factor, or sensor balance, the means of the amplitudes of the two signals are made to be the same (515). The gain factor may be based on the ratio of the amplitudes of the signals from the first and second motion sensors 205. In the example process 500, the amplitude of the signal from the second sensor 205 is multiplied by the sensor balance to ensure that the means of the amplitudes of the two signals are the same (520). A sensor difference signal is determined by subtracting the amplitude signal from the first sensor 205 from the weighted amplitude signal from the second sensor 205 (525).

A band pass filter is applied to the sensor difference signal to emphasize the portion of the sensor difference signal within the frequency range that is known to include the beat frequency (530). The frequency range that includes the beat frequency may be determined by considering the variation of the driven mode frequency and the Coriolis mode frequency over the full density range of the meter. For example, the meter may be designed to determine the density of a wide range of materials. The meter may be used to determine the density of low-density fluids and materials, such as air, as well as higher density fluids and materials, such as water or a cement slurry. In some implementations, the frequency at which the bandpass filter is centered may be determined, at least in part, by physical characteristics of the flowtube. For example, a flowtube having a cross-sectional diameter of 6" (15.2 centimeters) has a beat frequency between 9 Hz and 11 Hz. The bandbass filter may be designed to capture the beat frequency associated with such a flowtube.

Zero crossing techniques may be used to track the frequency of the beat signal (535) and a raw beat frequency is produced (540). Alternatively, Fourier analysis of the beat signal may be used to determine the beat frequency. Finally, filtering may be applied to reduce noise in the beat frequency estimate (545). The Coriolis mode frequency may be calculated from the difference between the beat frequency and the driven mode frequency (550).

Figure 6:
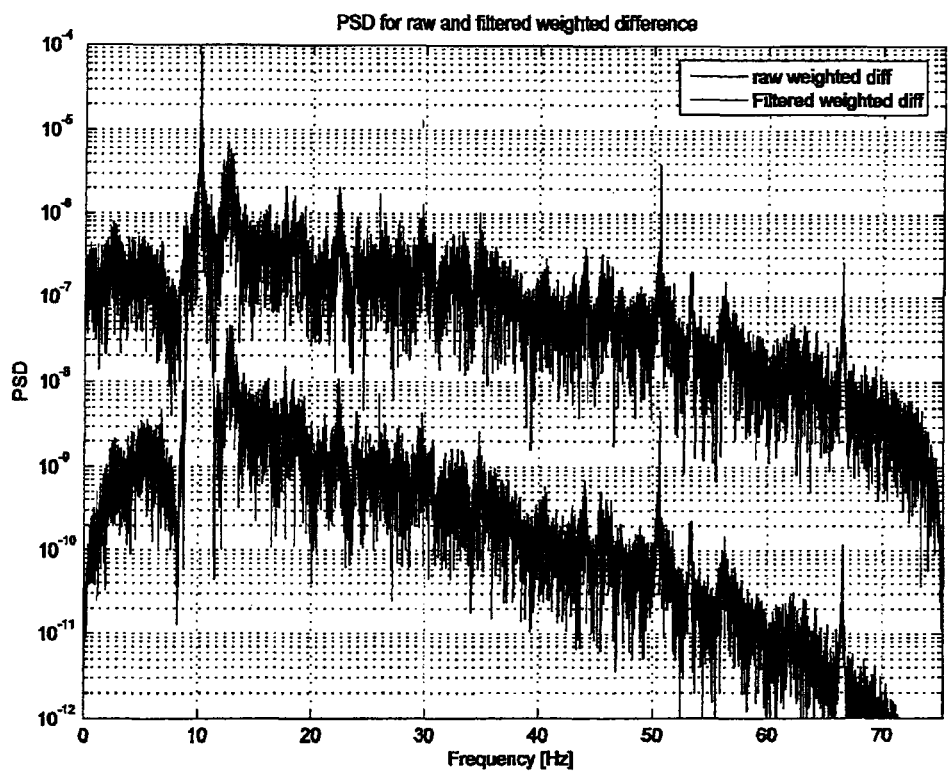
FIG. 6 is an example power spectra of a difference signal.

FIG. 6 shows a plot of the PSD of the sensor difference signal before and after the sensor difference signal is filtered with the band pass filter described above. The dominant peak in the PSD is the beat frequency. FFT analysis of this data gives an estimate of the peak frequency of 10.2145 Hz. This estimate is very similar to the beat frequency calculated from the difference of the modes in the sensor data spectrum discussed above. While the beat frequency dominates the unfiltered spectrum, other peaks may be present in the unfiltered spectrum that may introduce noise in the estimate of the beat frequency. However, filtering the spectrum with a band pass filter may reduce those frequency components not in the range of possible beat frequencies, thereby improving the resulting estimate of the beat frequency. The band pass filter may be implemented using an elliptical filter. Bandpass filtering also may remove any DC offset present in the sensor difference signal. The data shown in FIG. 6 was measured from a system that included a 6" meter. It is known that for 6" meter, the beat frequency will vary between 9 Hz and 11 Hz. Thus, the bandpass filter applied to the data from the 6" meter may be designed accordingly. For other meters, the expected beat frequency may be different, thus a bandpass filter with a different frequency band may be used.

Figure 7A:
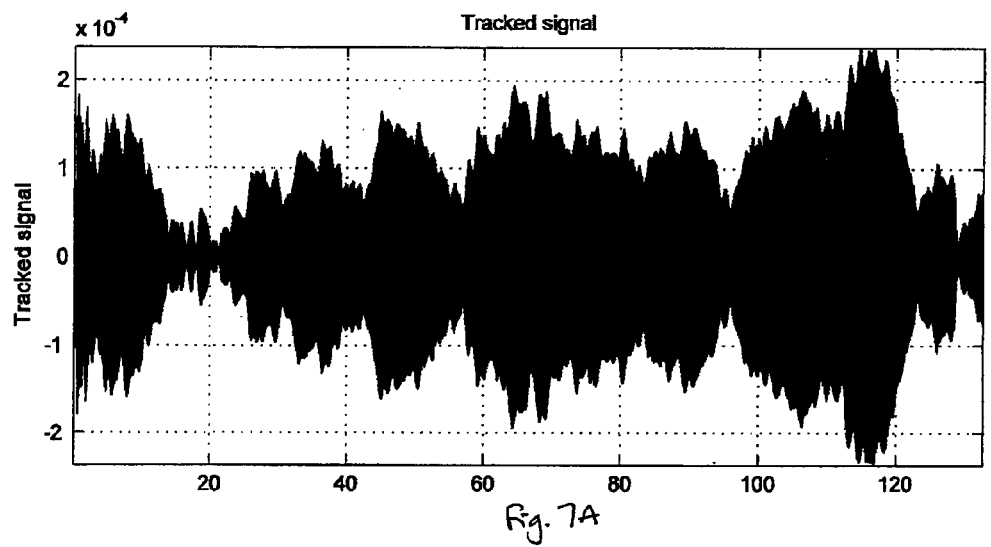
FIGS. 7A and 8A show examples of a filtered difference signal.
Figure 7B:
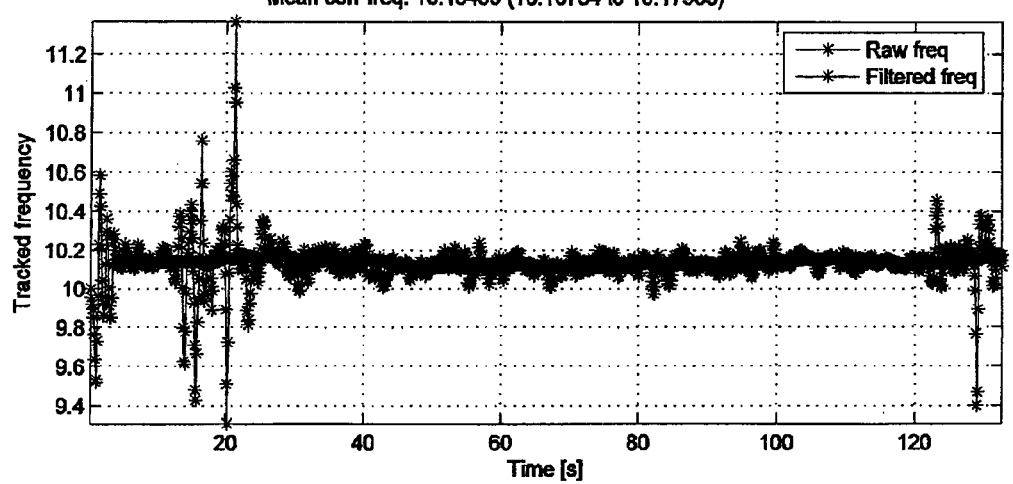
FIGS. 7B and 8B show examples of estimated beat frequency as a function of time.

FIGS. 7A and 7B show an overview of how the algorithms described above with respect to FIGS. 4 and 5 may be applied to a given data set. FIG. 7A shows the sensor difference signal after it is filtered with the bandpass filter. This filtered sensor difference signal is tracked using a zero crossing algorithm, as described in more detail below. FIG. 7B shows the raw and filtered estimated beat frequency as a function of time. The time between zero crossings of the filtered sensor difference signal gives an estimate of the beat frequency. However, as shown by the raw estimated beat frequency, the estimate of the beat frequency also may include noise, particularly if the amplitude of the different signal is small (e.g. between t=15 s and t=25 s). Thus, further filtering of this signal may improve the estimate of the beat frequency from which the Coriolis frequency may be derived.

Figure 8A:
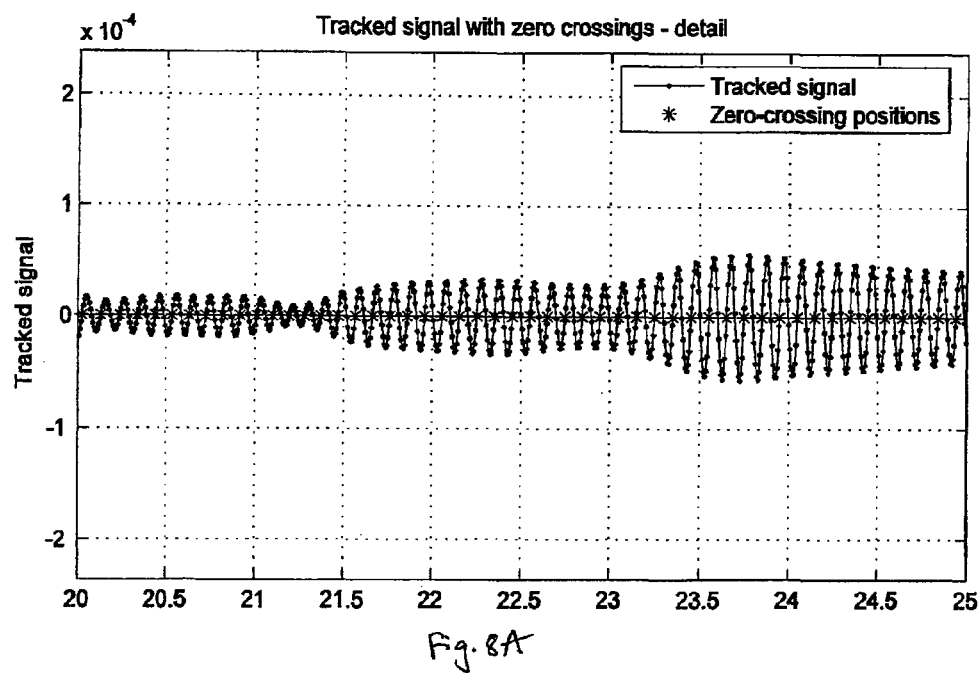
Figure 8B:
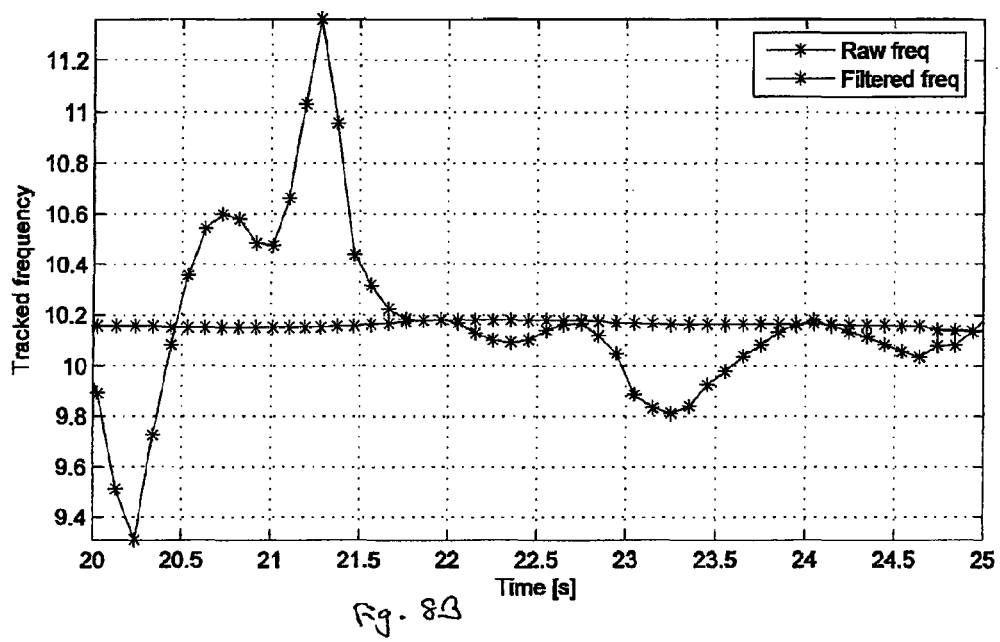

FIGS. 8A and 8B show the same data as FIGS. 7A and 7B, but in more detail and over a limited time period. As the tracked signal, shown in FIG. 8A, crosses zero or the x-axis, (e.g., the zero crossings), interpolation techniques may be used to estimate the exact zero crossing point. The interpolation techniques may include linear or cubic interpolation. An estimate of the beat frequency may be made based on the time between consecutive zero crossings. In other implementations, an estimate of the beat frequency may be made based on the time between non-consecutive zero-crossings. For example, more the estimate of the beat frequency may be made based on multiple zero-crossings occurring during a time period. Other techniques, such as Fourier methods, may be used to estimate the beat frequency from these signals.

Referring now to FIGS. 7A and 7B, when the amplitude of the sensor difference signal is small, the beat frequency estimate may vary considerably. For example, and as seen in more detail in FIG. 8A, the amplitude of the difference signal is small at approximately 20 seconds. The corresponding estimates of the beat frequency shown in FIGS. 7B and 8B vary considerably.

In order to improve the estimate of the beat frequency, a series of rules and/or filters may be applied to the filtered sensor difference signal. For example, the rules may include a rule specifying that frequency estimates based upon a sensor difference signal below a certain amplitude threshold be ignored. In another example, a rule may specify that if the observed frequency falls outside the passband of the bandpass filter, then that frequency is ignored. In addition to such rules, or alternatively, filters may be used to improve the beat frequency estimate. For example, a median filter may be used to remove minima in the difference signal. A median filter returns, for a given window size, the median value within the window. Thus, the median filter determines the middle value of the data in the window after sorting the data from highest to lowest. A median filter may thus act to remove low and high values from the data in the window without affecting the mean value of the output. Additionally, further filtering may be provided by applying an averaging filter to the output of the median filter.

Using the techniques described above with the data sets illustrated, a mean estimate of the beat frequency was determined to be 10.13499 Hz, as compared to 10.2145 Hz obtained based on an FFT of the beat frequency data. This beat frequency estimate lead to a Coriolis mode frequency estimate of 65.248 Hz based upon a difference between the determined beat frequency and the observed driven mode frequency. In comparison, the sensor FFT estimate was 65.1657 Hz, which, when compared to the 65.248 Hz using the beat frequency, results in the beat frequency tracking techniques being accurate to about 0.13%. Thus, the techniques described above may be used to determine a beat frequency estimate, and hence an estimate of the Coriolis frequency, without performing FFT analysis on the sensor difference signal.

A number of implementations have been described. Nevertheless, it will be understood that various modifications may be made. Accordingly, other implementations are within the scope of the following claims.

What is claimed is:

1. A Coriolis flowmeter comprising:
a conduit configured to receive a fluid flowing through the conduit;
a driver positioned to drive motion of the conduit, the motion of the conduit including a driven mode of vibration and a Coriolis mode of vibration when the fluid is flowing through the conduit, the driver driving the conduit in the driven mode of vibration and the Coriolis mode of vibration arising from forces associated with the fluid flowing through the conduit while the driver is driving the conduit in the driven mode of vibration;
a first sensor positioned to sense motion of the conduit at a first location and output a first sensor signal indicative of the motion of the conduit at the first location;
a second sensor positioned to sense motion of the conduit at a second location and output a second sensor signal indicative of the motion of the conduit at the second location, the second location being different from the first location; and
a controller configured to:
operate the driver;
determine a frequency of the Coriolis mode of vibration based on a beat frequency produced by interaction between the driven mode of vibration and the Coriolis mode of vibration while the driver is driving motion of the conduit and the fluid is flowing through the conduit; and
determine a mass flow rate of the fluid flowing through the conduit based on the determined frequency of the Coriolis mode of vibration.

2. A Coriolis flowmeter as set forth in claim 1 wherein said controller is further configured to determine a beat signal by analyzing amplitudes of the first and second sensor signals, the beat frequency being the frequency of the beat signal.

3. A Coriolis flowmeter as set forth in claim 2 wherein said controller is further configured to determine the beat frequency by: (i) determining a first time at which the amplitude of the beat signal has a predefined value and a second time at which the amplitude of the beat signal has the predefined value; (ii) determining a difference between the first and second times; and (3) determining the beat frequency based on said difference.

4. A Coriolis flowmeter as set forth in claim 3 wherein the predefined value is zero.

5. A Coriolis flowmeter as set forth in claim 4 wherein the first time is at first occurrence of the predefined value and the second time is at a second occurrence of the predefined value, and the first and second occurrences are nonconsecutive occurrences of the predefined value.

6. A Coriolis flowmeter as set forth in claim 1 wherein using the beat frequency to determine the frequency of the Coriolis mode comprises determining a difference between the beat frequency and a frequency of the driven mode.

7. A Coriolis flowmeter as set forth in claim 3 wherein using the beat frequency to determine the frequency of the Coriolis mode comprises determining a difference between the beat frequency and a frequency of the driven mode.

8. A Coriolis flowmeter as set forth in claim 7 wherein the first time is at first occurrence of the predefined value and the second time is at a second occurrence of the predefined value, and the first and second occurrences are nonconsecutive occurrences of the predefined value.

\* \* \* \* \*